United States Patent [19]

Stecher et al.

[11] Patent Number: 5,314,894
[45] Date of Patent: May 24, 1994

[54] (S)-(+)-HYDROXYCHLOROQUINE

[75] Inventors: Vera J. Stecher, Dobbs Ferry; William F. Michne, Poestenkill, both of N.Y.

[73] Assignee: Sterling Winthrop Inc., New York, N.Y.

[21] Appl. No.: 945,032

[22] Filed: Sep. 15, 1992

[51] Int. Cl.$^5$ ..................... A61K 31/47; C07D 215/38
[52] U.S. Cl. ................................. 514/313; 514/825; 514/895; 546/163
[58] Field of Search ............... 546/163; 514/313, 895, 514/825

[56] References Cited

U.S. PATENT DOCUMENTS 2,546,658  3/1951  Surrey .................................. 546/163
5,021,426  6/1991  Baldwin ............................... 514/895

OTHER PUBLICATIONS

A. J. McLachlan et al., J. Chromatogr., 570 (No. 1), 119-127 (Sep. 18, 1991).
J. Iredale et al., J. Chromatogr., 573 (No. 2), 253-258 (Jan. 17, 1992).
S. E. Tett et al., Br. J. Clin. Pharmac., 26, 303-313 (1988).
Chem. Abstr. 92, 69587p (1980) (Haberkorn).
Chem. Abstr. 90, 132863b (1979) (Fink).
J. C. Craig et al., J. Org. Chem., 53, 1167-1170 (1988).
G. Blaschke et al., Chem. Ber., 111, 2732-2734 (1978) (+English translation).
H. N. Bernstein, Annals of Ophthalmology, 23, 292-296 (1991).

*Primary Examiner*—Marianne M. Cintins
*Assistant Examiner*—Catherine S. Kilby Scalzo
*Attorney, Agent, or Firm*—Liza D. Hohenschutz; William J. Davis

[57] ABSTRACT (S)-(+)-Hydroxychloroquine substantially free of (R)-(−)-hydroxychloroquine, or a pharmaceutically acceptable acid-addition salt thereof and a method of use thereof and a composition containing it for the treatment of malaria, lupus erythematosus or rheumatoid arthritis.

12 Claims, No Drawings ns
(S)-(+)-HYDROXYCHLOROQUINE

BACKGROUND OF THE INVENTION (a) Field of the Invention

The invention relates to (S)-(+)-2-[[4-[(7-chloro-4-quinolinyl)amino]pentyl]ethylamino]ethanol [hereafter (S)-(+)-hydroxychloroquine] which is useful in the treatment of acute attacks and suppression of malaria due to Plasmodium vivax, Plasmodium malariae, Plasmodium ovale and susceptible strains of Plasmodium falciparum, systemic and discoid lupus erythematosus, and rheumatoid arthritis.

(b) Information Disclosure Statement

Racemic hydroxychloroquine, which is 2-[[4-[(7-chloro-4-quinolinyl)amino]pentyl]ethylamino]ethanol (Surrey U.S. Pat. No. 2,546,658, Mar. 27, 1951), and which is sold as the sulfate salt by Sanofi Winthrop Pharmaceuticals under the tradename Plaquenil ® Sulfate, is primarily useful as an antimalarial agent and is also used in treating lupus erythematosus and rheumatoid arthritis.

A. J. McLachlan et al., J. Chromatogr., 570 (No. 1), 119-127, dated Sep. 18, 1991, disclose the high-performance liquid chromatographic separation of the enantiomers of hydroxychloroquine and its major metabolites in biological fluids. The authors acknowledge a gift of S(+)-hydroxychloroquine from Sterling Pharmaceuticals.

J. Iredale et al., J. Chromatogr., 573 (No. 2), 253-258, dated Jan. 17, 1992, disclose the development of a sequential achiral-chiral high-performance liquid chromatographic system for the determination of the enantiomers of hydroxychloroquine and its three major metabolites.

S. E. Tett et al., Br. J. Clin. Pharmac., 26, 303-313 (1988), disclose a dose-ranging study of the pharmacokinetics of racemic hydroxychloroquine following intravenous administration to healthy volunteers. The authors state that the pharmacokinetics of hydroxychloroquine are similar to those of chloroquine.

Chem. Abstr. 92, 69587p (1980) discloses that when administered orally daily for four days beginning at two hours after Plasmodium berger infestation in mice, doses of 5 and 20 mg/kg of the d-enantiomer of chloroquine diphosphate were more effective than corresponding doses of the 1-enantiomer in antimalarial parameters measured, including percentage of cured mice at >7.5 mg/kg; and that the d-enantiomer was also more active than the racemate, but only at subcurative doses.

Chem. Abstr. 90, 132863b (1979) discloses the results of a study of the activity of chloroquine enantiomers against rodent malaria in which it was found that (+)-chloroquine diphosphate was a more active antiplasmodial agent than (−)-chloroquine diphosphate in Plasmodium vinckei-infected mice, and that the activity of (±)-chloroquine diphosphate was between that the two enantiomers.

J. C. Craig et al., J. Org. Chem., 53, 1167-1170 (1988), disclose the absolute configuration of the enantiomers of chloroquine and the synthesis of (R)-(−)-chloroquine by condensation of (R)-(−)-4-amino-1-(diethylamino)pentane of >90% purity with 4,7-dichloroquinoline.

G. Blaschke et al., Chem. Ber., 111, 2732-2734 (1978) disclose the chromatographic separation of the enantiomers of chloroquine as well as their preparation by condensation of (+) and (−)-4-amino-1-(diethyamino)pentane with 4,7-dichloroquinoline.

H. N. Bernstein, Annals of Ophthalmology, 23, 292-296 (1991), presents an analysis of all published cases and Food and Drug Administration reports of retinopathy induced by hydroxychloroquine. The author states that antimalarial therapy, because of a relative lack of systemic side effects compared with other immunomodulating drugs, has been used increasingly over the past 15 years for the treatment of rheumatoid arthritis, discoid and systemic lupus erythematosus, and other predominantly autoimmune disease, and that in the United States, hydroxychloroquine is preferred to chloroquine because it is considered significantly less retinotoxic at the current recommended maximum dose (400 mg/day, according to the FDA and the manufacturer). The author nevertheless notes that physicians are concerned about using drugs with retinotoxic potential at higher dose levels. He then suggests, inter alia, that the risk of true retinopathy is nullified when the maintenance daily dose is based on $\leq 6.5$ mg/kg body weight and states that even in the absence of a real toxicity risk, it is recommended that a periodic ocular examination program be followed because of the retinotoxic history associated with hydroxychloroquine.

SUMMARY OF THE INVENTION

Drugs having an asymmetric center are, in most instances, administered as racemates consisting of a 1:1 mixture of two enantiomers. However, since there often are pharmacodynamic and pharmacokinetic differences between the two enantiomers, therapeutic efficacy may reside entirely or for the most part in one of the two enantiomers and therefore may be diluted by the other enantiomer in the racemate and, moreover, any adverse effect which may be associated with the racemate may be attributable to the other enantiomer. In such cases it would be desirable to administer the single enantiomer in which the therapeutic efficacy resides.

Plaquenil ® Sulfate (hydroxychloroquine sulfate) is a racemic mixture (1:1) of 2 enantiomers. The manufacturer of this drug contraindicates its use, inter alia, in the presence of retinal or visual field changes attributable to any 4-aminoquinoline compound and warns that irreversible retinal damage has been observed in some patients who had received long term or high-dosage 4-aminoquinoline therapy for discoid and systemic lupus erythematosus or rheumatoid arthritis and notes that retinopathy has been reported to be dose-related. Adverse reactions discussed by the manufacturer include a small number of cases of retinal changes which have been reported as occurring in patients who received only hydroxychlorquine.

Although Plaquenil ® Sulfate has an excellent ocular safety record when the maintenance dose levels recommended by the manufacturer (310 mg base/day) for the treatment of malaria, discoid and systemic lupus erythematosus and rheumatoid arthritis are not exceeded, nevertheless, because cases of retinal changes in patients receiving only hydroxychloroquine have been reported and physicians are concerned about using drugs with retinotoxic potential at higher doses (see H. N. Bernstein, supra), it would be highly desirable if the risk of retinopathy in the use of hydroxychloroquine could be substantially reduced, particularly for that segment of the population which could benefit from hydroxychloroquine therapy but where such therapy is contraindicated because of the presence of retinal or visual field changes attributable to any 4-aminoquinoline compound.

Unexpectedly, it has now been found that when (S)-(+)-hydroxychloroquine and its (R)-(−)-antipode were compared in the Rat Pleurisy Macrophage Model, which model is used to identify disease modifying antirheumatic drugs [see Z. E. Mielens et al., J. Rheumatol., 12, 1083–1087 (1985)], (S)-(+)-hydroxychloroquine was approximately 70% more active than the corresponding (R)-(−)-enantiomer in decreasing the accumulation of cells (monocytes) to the pleural cavity. Furthermore, it was found that in a study wherein racemic hydroxychloroquine was administered either intravenously, subcutaneously or orally to rabbits, there was an enantioselective accumulation of (R)-(−)-hydroxychloroquine in the ocular tissue. The ratio of the (R)-(−)-enantiomer to the (S)-(+)-enantiomer in this study was 1.58±0.24. These results were consistent with the results of pharmacokinetic studies in humans treated with racemic hydroxychloroquine in which it was found that for (R)-(−)-hydroxychloroquine, the fraction absorbed was approximately two times greater, the systemic clearance was more than two fold greater and the apparent half life was significantly faster than for the corresponding (S)-(+)-enantiomer. These differences are attributed to enantioselective distribution into various tissue compartments such as the retina.

These unexpected discoveries have important clinical implications for hydroxychloroquine therapy in that malaria, lupus erythematosus and rheumatoid arthritis may now be effectively treated with (S)-(+)-hydroxychloroquine substantially free of (R)-(−)-hydroxychloroquine with concomitant lower adverse effects attributable to the corresponding (R)-(−)-enantiomer with the result that it will be possible, where indicated, to administer (S)-(+)-hydroxychloroquine at higher dose levels and/or longer periods of times than is now recommended for administration of equivalent dose levels of racemic hydroxychloroquine.

Therefore, in one aspect of the invention there is provided (S)-(+)-hydroxychloroquine substantially free of (R)-(−)-hydroxychloroquine, or a pharmaceutically acceptable acid-addition salt thereof.

In another aspect there is provided a method for the treatment of malaria, lupus erythematosus or rheumatoid arthritis in a human which comprises administering to the human an amount effective to treat malaria, lupus erythematosus or rheumatoid arthritis of (S)-(+)-hydroxychloroquine substantially free of (R)-(−)-hydroxychloroquine or a pharmaceutically acceptable acid-addition salt thereof.

In another aspect the invention provides a composition for treating malaria, lupus erythematosus or rheumatoid arthritis in a human comprising (S)-(+)-hydroxychloroquine substantially free of (R)-(−)-hydroxychloroquine or a pharmaceutically acceptable acid-addition salt thereof in an amount effective for the treatment of malaria, lupus erythematosus or rheumatoid arthritis and a pharmaceutically acceptable vehicle.

DETAILED DESCRIPTION OF THE INVENTION INCLUSIVE OF THE PREFERRED EMBODIMENTS

Preparation of (S)-(+)-Hydroxychloroquine (S)-(+)-Hydroxychloroquine was prepared by condensing (S)-(+)-2-[(4-aminopentyl)ethylamino]ethanol with 4,7-dichloroquinoline. The latter compound is known. The (S)-(+)-2-[(4-aminopentyl)ethylamino]ethanol was prepared by resolving known racemic 2-[(4-aminopentyl)ethylamino]-ethanol by forming a salt thereof with known (S)-(+)-mandelic acid and separating the (S)-(+)-mandelic acid salts of the two enantiomers by crystallization.

The following example illustrates the method of preparation.

EXAMPLE a) (S)-(+)-2-[(4-Aminopentyl)ethylamino]ethanol

A solution of (S)-(+)-mandelic acid (15.9 g, 105 mmol, 0.60 equivalents) in ethyl alcohol was added to a solution of racemic 2-[(4-aminopentyl)ethylamino]ethanol (30.37 g, 174 mmol, 1.00 equivalents) in ethyl ether. The solvents were evaporated and the resulting white solid was recrystallized from ethyl alcohol, washed with a little ethyl ether, recrystallized again from ethyl alcohol and washed with a little ethyl alcohol and then ethyl ether. The crystals were dried in vacuo overnight to give 7.45 g of salt of the title compound with (S)-(+)-mandelic acid, m.p. 126°–127° C. This salt was dissolved in water and the resulting solution was made basic with 35% sodium hydroxide and extracted three times with methylene chloride. The combined extracts were dried ($K_2CO_3$), filtered and evaporated. The residue was distilled (Kugelrohr; 80°–100° C./0.020 torr) to yield the title compound as a colorless oil (approximately 3.7 g) which was used as such in the next step.

b) (S)-(+)-Hydroxychloroquine

A mixture of the product from (a) above (approximately 3.7 g, 19.0 mmol, 1.00 equivalents), N-ethyldiisopropylamine (2.45 g, 20.9 mmol, 1.10 equivalents) and 4,7-dichloroquinoline (3.31 g, 19.0 mmol, 1.00 equivalents) was heated at reflux under nitrogen for 48 hours and cooled. The excess base was poured off and the residue was taken up in methyl alcohol and excess aqueous sodium hydroxide. The mixture was diluted with water and extracted three times with methylene dichloride. The combined organic extracts were washed two times with water, once with brine, dried ($K_2CO_3$), filtered and evaporated to dryness. The residue was filtered through silica gel with tetrahydrofuran:diethylamine (95:5) to give 4.12 g of material. This material was subjected to fractional distillation (Kugelrohr). A white crystalline solid was obtained at approximately 130° C. and 0.010 torr. The receiver bulb was changed and the distillation temperature was increased to approximately 200° C. This provided 2.93 g of the title compound which was converted to its sulfate salt by treatment with one equivalent of 1 molar sulfuric acid in methyl alcohol and evaporation to a sticky oil. The oily salt was dissolved in 5 ml of methyl alcohol and acetone was added slowly until the solution turned a little murky. This solution was allowed to stand overnight at room temperature and the resulting crystalline salt was collected and washed with acetone and dried at 50° C. (0.01 torr) for twenty-four hours to give approximately 390 mg of (S)-(+)-hydroxychloroquine sulfate as an off-white solid, m.p. 235°–238° C.(dec.); $[\alpha]_D = +105.9$ (1% in $H_2O$). It was determined by direct chromatographic resolution via high performance liquid chromatography using a chiral stationary phase that this material contained 98.4% by weight of the (S)-(+)-enantiomer and 1.6% by weight of the (R)-(−)-enantiomer.

In order to avoid or minimize adverse effects associated with the enantioselective accumulation of (R)-(—)-hydroxychloroquine in ocular tissue, it is preferable in practicing the invention to use as the active ingredient (S)-(+)-hydroxychloroquine substantially free of (R)-(—)-hydroxychloroquine. In this context, the expression "substantially free" means that the active ingredient should contain at least 90% by weight of (S)-(+)-hydroxychloroquine and 10% by weight or less of (R)-(—)-hydroxychloroquine, preferably at least 95% by weight of the (S)-(+)-enantiomer and 5% by weight or less of the (R)-(—)-enantiomer and more preferably at least 98% by weight and 2% by weight or less of the (R)-(—)-enantiomer. Ideally the (S)-(+)-hydroxychloroquine should be free of (R)-(—)-hydroxychloroquine.

Included within the purview of this invention in addition to (S)-(+)-hydroxychloroquine are its pharmaceutically acceptable acid-addition salts such as those derived from nontoxic inorganic acids, including hydrochloric acid, sulfuric acid, sulfamic acid and the like, and nontoxic organic acids, including tartaric acid, citric acid, acetic acid and the like.

The composition of the invention can be formulated for oral or parenteral administration in solid, liquid or other appropriate dosage forms including tablets, capsules and solutions, using conventional pharmaceutically acceptable vehicles and techniques.

What is claimed is:

1. (S)-(+)-2-[[4-[(7-chloro-4-quinolinyl)amino]pentyl]ethylamino]ethanol substantially free of (R)-(—)-2-[[4-[(7-chloro-4-quinolinyl)amino]pentyl]ethylamino]ethanol, or a pharmaceutically acceptable acid-addition salt thereof.

2. (S)-(+)-2-[[4-[(7-chloro-4-quinolinyl)amino]pentyl]ethylamino]ethanol substantially free of (R)-(—)-2-[[4-[(7-chloro-4-quinolinyl)amino]pentyl]ethylamino]ethanol according to claim 1 wherein the weight ratio of (S)-(+)-2-[[4-[(7-chloro-4-quinolinyl)amino]pentyl]ethylamino]ethanol to (R)-(—)-2-[[4-[(7-chloro-4-quinolinyl)amino]pentyl]ethylamino]ethanol is at least 95:5.

3. (S)-(+)-2-[[4-[(7-chloro-4-quinolinyl)amino]pentyl]ethylamino]ethanol substantially free of (R)-(—)-2-[[4-[(7-chloro-4-quinolinyl)amino]pentyl]ethylamino]ethanol according to claim 2 wherein the weight ratio of (S)-(+)-2-[[4-[(7-chloro-4-quinolinyl)amino]pentyl]ethylamino]ethanol to (R)-(—)-2-[[4-[(7-chloro-4-quinolinyl)amino]pentyl]ethylamino]ethanol is at least 98:2.

4. A method of treating malaria, lupus erythematosus or rheumatoid arthritis in a human which comprises administering to the human an amount effective to treat malaria, lupus erythematosus or rheumatoid arthritis of (S)-(+)-2-[[4-[(7-chloro-4-quinolinyl)amino]pentyl]ethylamino]ethanol substantially free of (R)-(—)-2-[[4-[(7-chloro-4-quinolinyl)amino]pentyl]ethylamino]ethanol, or a pharmaceutically acceptable acid-addition salt thereof.

5. A method according to claim 4 wherein, in the (S)-(+)-2-[[4-[(7-chloro-4-quinolinyl)amino]pentyl]ethylamino]ethanol substantially free of (R)-(—)-hydroxychloroquine, the weight ratio of (S)-(+)-2-[[4-[(7-chloro-4-quinolinyl)amino]pentyl]ethylamino]ethanol to (R)-(—)-2-[[4-[(7-chloro-4-quinolinyl)amino]pentyl]ethylamino]ethanol is at least 95:5.

6. A method according to claim 5 wherein the weight ratio of (S)-(+)-2-[[4-[(7-chloro-4-quinolinyl)amino]pentyl]ethylamino]ethanol to (R)-(—)-2-[[4-[(7-chloro-4-quinolinyl)amino]pentyl]ethylamino]ethanol is at least 98:2.

7. A method according to claim 4 for treating rheumatoid arthritis.

8. A method according to claim 4 wherein the route of administration is oral.

9. A composition for treating malaria, lupus erythematosus or rheumatoid arthritis in a human comprising (S)-(+)-2-[[4-[(7-chloro-4-quinolinyl)amino]pentyl]ethylamino]ethanol substantially free of (R)-(—)-2-[[4-[(7-chloro-4-quinolinyl)amino]pentyl]ethylamino]ethanol, or a pharmaceutically acceptable acid-addition salt thereof in an amount effective for the treatment of malaria, lupus erythematosus or rheumatoid arthritis and a pharmaceutically acceptable vehicle.

10. A composition according to claim 9 wherein, in the (S)-(+)-2-[[4-[(7-chloro-4-quinolinyl)amino]pentyl]ethylamino]ethanol substantially free of (R)-(—)-2-[[4-[(7-chloro-4-quinolinyl)amino]pentyl]ethylamino]ethanol, the weight ratio of (S)-(+)-2-[[4-[(7-chloro-4-quinolinyl)amino]pentyl]ethylamino]ethanol to (R)-(—)-2-[[4-[(7-chloro-4-quinolinyl)amino]pentyl]ethylamino]ethanol is at least 95:5.

11. A composition according to claim 10 wherein the weight ratio of (S)-(+)-2-[[4-[(7-chloro-4-quinolinyl)amino]pentyl]ethylamino]ethanol to (R)-(—)-2-[[4-[(7-chloro-4-quinolinyl)amino]pentyl]ethylamino]ethanol is at least 98:2.

12. A composition according to claim 9 formulated for oral administration.

* * * * *